United States Patent
Tuchschmid et al.

(10) Patent No.: US 8,992,230 B2
(45) Date of Patent: Mar. 31, 2015

(54) MEDICAL TRAINING SYSTEMS AND METHODS

(71) Applicants: Virtamed AG, Zurich (CH); Eidgenossische Technische Hochschule Zurich, Zurich (CH)

(72) Inventors: Stefan Tuchschmid, Zurich (CH); Daniel Bachofen, Winterthur (CH); Matthias Harders, Zurich (CH); Jonas Spillmann, Zurich (CH)

(73) Assignees: Virtamed AG, Zurich (CH); Eidgenossische Technische Hochschule Zurich, Zurich (CH)

( * ) Notice: Subject to any disclaimer, the term of this patent is extended or adjusted under 35 U.S.C. 154(b) by 106 days.

(21) Appl. No.: 13/732,899

(22) Filed: Jan. 2, 2013

(65) Prior Publication Data
US 2013/0189663 A1    Jul. 25, 2013

Related U.S. Application Data

(60) Provisional application No. 61/589,714, filed on Jan. 23, 2012.

(51) Int. Cl.
G09B 23/28    (2006.01)

(52) U.S. Cl.
CPC ..................... G09B 23/28 (2013.01)
USPC ........................................................ 434/262

(58) Field of Classification Search
None
See application file for complete search history.

(56) References Cited

U.S. PATENT DOCUMENTS

| | | | |
|---|---|---|---|
| 3,947,974 A * | 4/1976 | Gordon et al. | 434/266 |
| 2005/0021043 A1* | 1/2005 | Jansen et al. | 606/102 |
| 2006/0194180 A1* | 8/2006 | Bevirt et al. | 434/262 |
| 2009/0305215 A1* | 12/2009 | Wilkins | 434/274 |
| 2010/0086905 A1 | 4/2010 | Illana Alejandro et al. | |
| 2010/0248200 A1 | 9/2010 | Ladak et al. | |
| 2012/0058457 A1* | 3/2012 | Savitsky | 434/262 |
| 2012/0220859 A1* | 8/2012 | Amiot et al. | 600/424 |

OTHER PUBLICATIONS

J.D. Mabrey et al., "Virtual Reality in Orthopaedics—Is It a Reality?", Clinical Orthopaedics and Related Research, vol. 468, No. 10, pp. 2586-2591, Oct. 2010.
L. Moody et al., "The Feasibility of a Mixed Reality Surgical Training Simulator", Virtual Reality, vol. 12, No. 2, pp. 77-86, May 2008.
R. Ziegler et al., "Virtual Reality Arthroscopy Training Simulator", Computers in Biology and Medicine, vol. 25, No. 2, pp. 193-203, Mar. 1995.
A.L. Fuhrmann et al., "Comprehensive Calibration and Registration Procedures for Virtual Reality", In Proc. Eurographics Workshop on Virtual Environments 2001, pp. 219-228 (2001).

* cited by examiner

*Primary Examiner* — Xuan Thai
*Assistant Examiner* — Michael Grant
(74) *Attorney, Agent, or Firm* — DLA Piper LLP US

(57) ABSTRACT

Simulation systems and methods may enable virtual imaging. A data processing unit may receive data from a calibration unit indicating a position and/or orientation of a position and orientation sensor relative to a physical model. The data processing unit may also receive data from the position and orientation sensor indicating a position and/or orientation of the physical model. The data processing unit may generate a virtual image using the data from the position and orientation sensor and the data from the calibration unit. The data processing unit may render the virtual image to a display.

43 Claims, 9 Drawing Sheets

MEDICAL TRAINING SYSTEMS AND METHODS

CROSS-REFERENCE TO RELATED APPLICATIONS

This application claims the benefit of U.S. Provisional Patent Application No. 61/589,714, filed Jan. 23, 2012, which is incorporated by reference in its entirety.

BACKGROUND

1. Field

The present invention relates to computerized medical simulation in general, and more specifically to virtual reality and/or augmented reality simulation devices and systems for medical training purposes.

2. Technical Background

Traditional medical procedures requiring invasive surgery are frequently being replaced by less invasive image-guided techniques taking advantage of modern imaging technologies, such as endoscopy, for both diagnostic and therapeutic purposes. These new techniques may require dedicated training for physicians and surgeons to master the indirect hand-eye coordination required by the imaging system as well as the manipulation of the imaging tools in addition to the conventional medical instruments and procedures. Computerized medical procedure training simulators may enable the physicians and trainees to develop and improve their practice in a virtual reality environment before actually practicing in the operation room.

Advanced medical procedure simulators may be based on a virtual reality ("VR") and/or a mixed or augmented reality ("AR") simulation apparatus by which the physician can experiment a medical procedure scenario. The VR/AR system may compute and display a visual VR/AR model of anatomical structures in accordance with physician gestures and actions to provide various feedback, such as visual feedback. In a VR system, an entire image may be simulated for display to a user, and in an AR system, a simulated image may be overlaid or otherwise incorporated with an actual image for display to a user. Various patient models with different pathologies can be selected. Therefore, natural variations as encountered over the years by practicing surgeons can be simulated for a user over a compressed period of time for training purposes. The medical simulation procedure can be recorded and rehearsed for evaluation purpose. The VR/AR simulation system can also compute and provide various metrics and statistics.

Some VR/AR simulation systems such as the one described in patent application US2010/0086905 include a human anatomy model of a joint of organ in real size and a simulated medical instrument that imitates the real medical procedure instrument. The model is further adapted with sensors and mobile members for guiding, tracking and controlling the medical instrument operation within the anatomy model. The simulated medical instrument is usually adapted from dedicated VR or AR hardware to provide haptic feedback, such as force feedback, to the physician to reproduce the instrument touch and feel sensing when touching the model.

Legacy medical VR/AR simulators often require dedicated haptic hardware such as, for instance, the two haptic devices arranged with a mobile member in the arthroscopy VR simulator described in U.S. patent application 2010/0086905. Those VR/AR simulators can require specific setup and calibration prior to be operated; they can be expensive; they may suffer a number of mechanical constraints, such as friction, and the maximal amount of forces and torques displayed may be insufficient to provide a realistic simulation. The degree of possible motion of the tools due to mechanical configuration of the device can be limited. Moreover, the setup can be unstable over time, thus requiring regular maintenance to avoid inducing training errors. Furthermore, for a multipurpose training room, many simulators may be required, as different anatomical features may require different simulators. For instance, a knee arthroscopy simulator and a pelvic simulator may require two different simulators to be set up and calibrated. Furthermore, in order to align a VR/AR computerized simulation visual feedback to an actual physical gesture and action of the simulation tools, the VR/AR system may require a calibration setup phase to position the VR/AR model relative to real world position and orientation of each simulated instrument before the simulator becomes operational. Wrong calibration should be carefully avoided as it can be a source of significant training errors, potentially harmful to patients in later real operations. As taught for instance by U.S. patent application 2010/0248200, the haptic device is therefore often manually calibrated by asking one or more experienced physician or medical residents to touch all virtual tissues using a virtual medical procedural tool, which may for example be a virtual blade, controlled by the haptic device.

The training tools described above can create significant budget and time overhead for the multipurpose training room operation, as multiple dedicated hardware devices may need to be installed in the room and skilled personnel may be required to operate the devices. Switching from one medical training procedure to another may be consequently cumbersome and time-consuming.

SUMMARY

Embodiments of flexible medical simulation apparatus, methods, and systems described herein may automatically adapt to various medical procedure training scenarios without requiring specialized hardware setup and calibration in the training room. A multipurpose medical procedure VR/AR simulator may be set up using an anatomy model comprising at least one position and orientation sensor and a calibration unit associated with such sensor. The calibration unit may store and transmit pre-computed calibration data associated with the sensor to the VR/AR simulator data processing unit. The data processing unit may compute and display an accurate VR/AR model in accordance with the anatomy model sensor position and orientation on the one hand and the VR/AR training scenario on the other hand. Accordingly, various VR/AR training scenarios corresponding to different patient pathologies can be simulated in a highly realistic way without requiring costly dedicated hardware integration, calibration, setup, and maintenance.

A multipurpose medical procedure VR/AR simulator may be setup with an interchangeable anatomy model comprising at least one position and orientation sensor and a calibration unit associated with such sensor and such model. The anatomy model may be plugged into the VR/AR simulator via a fast mount electrical and mechanical connection, for example. The calibration unit may store and transmit an anatomy model identification as well as pre-computed calibration data associated with the anatomy model sensor to the VR/AR simulator data processing unit. The data processing unit may compute and display an accurate VR/AR model in accordance with the anatomy model type, the sensor position and orientation, and the VR/AR training scenario. Accordingly, various VR/AR training scenarios corresponding to different anatomy models and different patient pathologies can be simulated in a highly realistic way without requiring a different medical procedure VR/AR simulator cart for each scenario or for some subsets of scenarios.

A medical procedure VR/AR simulator equipped with standard operating room tools comprising at least one position and orientation sensor and a calibration unit associated with such sensor and tool may facilitate the training of physicians. Each medical tool may have a sensor that may be plugged onto the VR/AR simulator via a standard, fast mount electrical and mechanical connection, for example. The calibration unit may store and transmit the tool identification as well as the pre-computed calibration data associated with the tool sensor to the VR/AR simulator data processing unit. The data processing unit may compute and display an accurate VR/AR model in accordance with the anatomy model type, each anatomy model sensor position and orientation, each tool type, each tool sensor position and orientation, and/or the VR/AR training scenario. Accordingly, various VR/AR training scenarios corresponding to different anatomy models, different patient pathologies, and/or different medical tools can be simulated in a highly realistic way with real tools. Moreover, different medical tools can be adapted to the VR/AR simulator at any time without requiring costly dedicated hardware integration, calibration, setup, and maintenance by highly skilled personnel.

The daily operation and maintenance of a VR/AR simulation training room may be facilitated by applying relative sensor position and orientation measurement to avoid cumbersome VR/AR simulator sensors calibration. To this end, more sensors than are theoretically needed for a full determination of the VR/AR model orientation and position may be employed in order to combine and compute the relative positions and orientations of the sensors in addition to and/or instead of their absolute position and orientation.

DETAILED DESCRIPTION

Figure 1A:
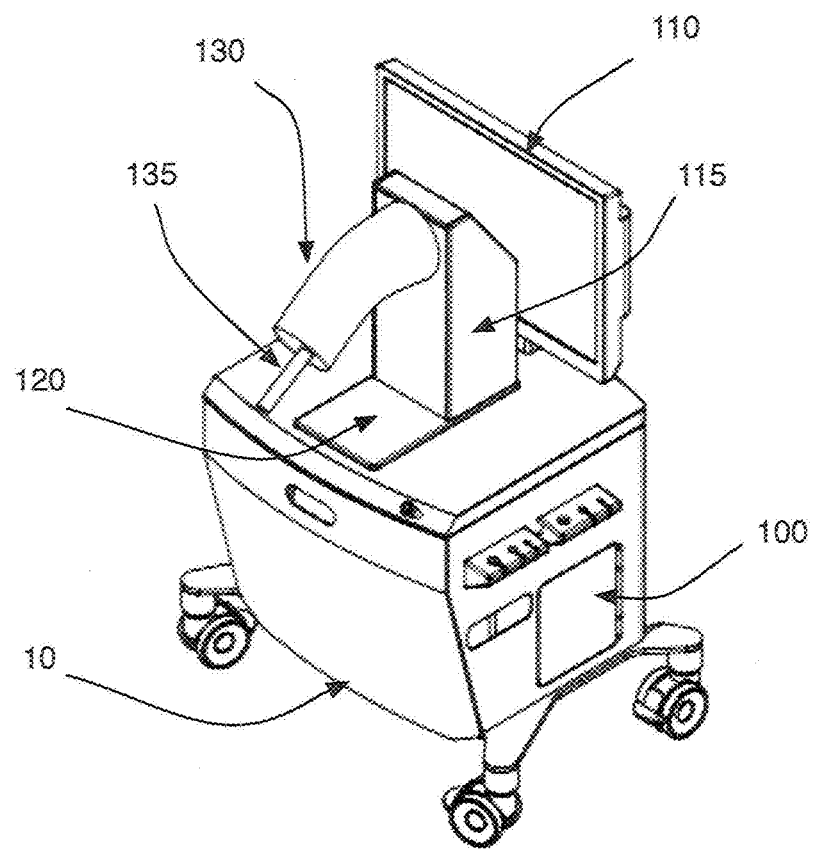
FIG. 1A illustrates a medical procedure VR/AR simulator cart hosting an anatomy model according to an embodiment of the invention.
Figure 1B:
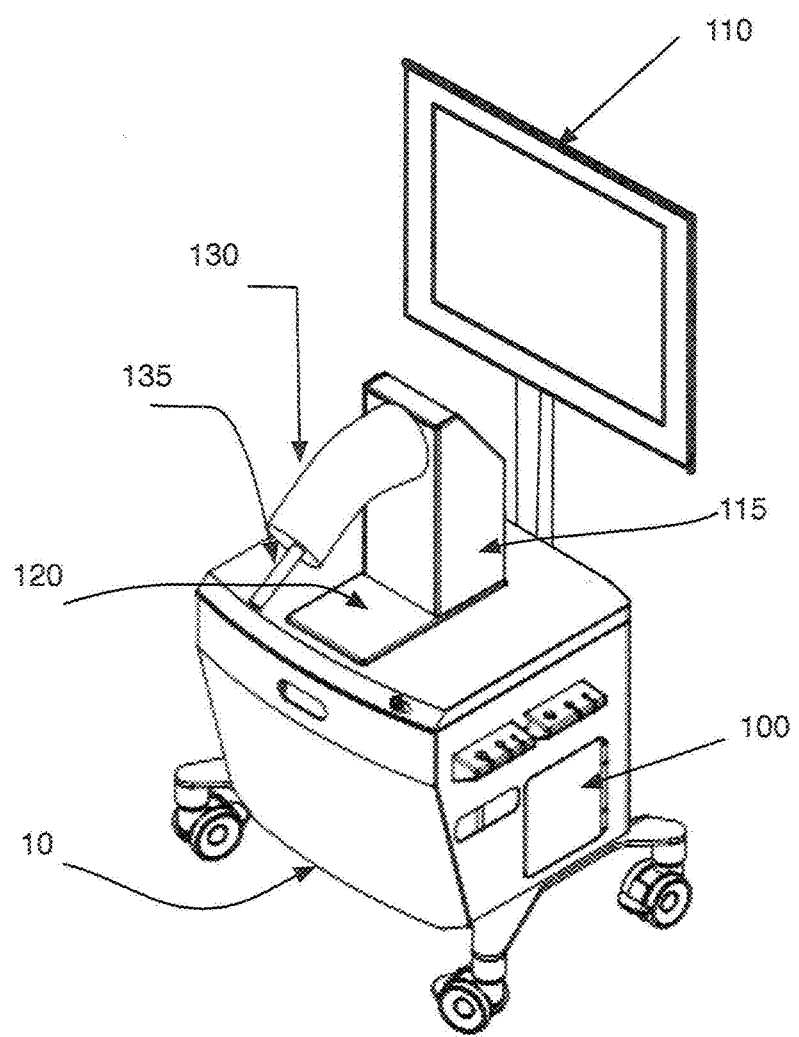
FIG. 1B illustrates a medical procedure VR/AR simulator cart hosting an anatomy model according to an embodiment of the invention.

FIGS. 1A-1B represent a medical procedure VR/AR simulator cart 10 comprising a data processing unit 100, a display screen 110, and a plug 120 adapted to receive a human anatomy model 130, according to an embodiment of the invention. For the purpose of illustration, in FIGS. 1A-1B, a human anatomy model 130 of a knee joint is shown, but other models can be used as well. The human anatomy model 130 may be made of flexible plastic or any other suitable material. The knee model of FIGS. 1A-1B can be manipulated with the handle 135 to reproduce model motion and deformation. For example, the knee model 130 can be manipulated to simulate various leg flexion angles and/or various valgus-varus angles.

The anatomy model 130 may be fastened to the cart 10 in such a way that it may be easily plugged in and out, for instance by clipping it onto the cart, while reproducing a real organ position in the operating room. In the embodiment of FIGS. 1A-1B, the knee model 130 is fastened to a vertical mount 115 that is itself plugged onto the cart plug 120 so that it may simulate a position of a real organ in the operating room.

In the arthroscopy application field, in addition to the knee, other joint models may be used and interchanged with the human anatomy model 130, such as a shoulder model, a hip model, a wrist model, or an elbow model. Furthermore, in order to support other medical procedures than arthroscopy, other organ models may be interchanged with the anatomy model 130, such as a bladder, a womb, an upper torso, a lower torso, or a pelvic model. Other examples of models can be found in the catalogues of specialized anatomic model suppliers such as Limbs&Things, Bristol, UK. Some models may be representative of the human anatomy. Other models may be representative of an animal anatomy, e.g. for veterinary training purpose. Some models can be attached directly to the cart plug 120 without a vertical mount 115, for instance a lower torso or pelvic model. Other models may be fastened to a vertical mount 115 that is attached to the cart plug 120.

The data processing unit 100 may comprise a central processing unit ("CPU"), memory, controlling module, and/or communication module, for example. Other embodiments may include data processing units 100 with other configurations and combinations of hardware and software elements. A distributed data processing unit may be used. Some or all of the data processing unit 100 components may be used to compute and display onto a display screen 110 a VR/AR simulation model that may correspond to a chosen medical procedure training scenario. Multiple display screens may also be used. The display screen 110 may comprise a touch interface to provide an interface for a physician during a simulation exercise. FIG. 1A illustrates the display screen 110 in a lowered position, which may be suitable for storage or transport, for example. FIG. 1B illustrates the display screen 110 in a raised position, which may be suitable for operation during a medical training scenario, for example. In some embodiments, the display screen 110 may be configured such that it can be positioned in one or more positions or viewing angles in addition to those shown in FIGS. 1A-1B. In other embodiments (not illustrated) the simulator cart may further comprise a camera.

Figure 2A:
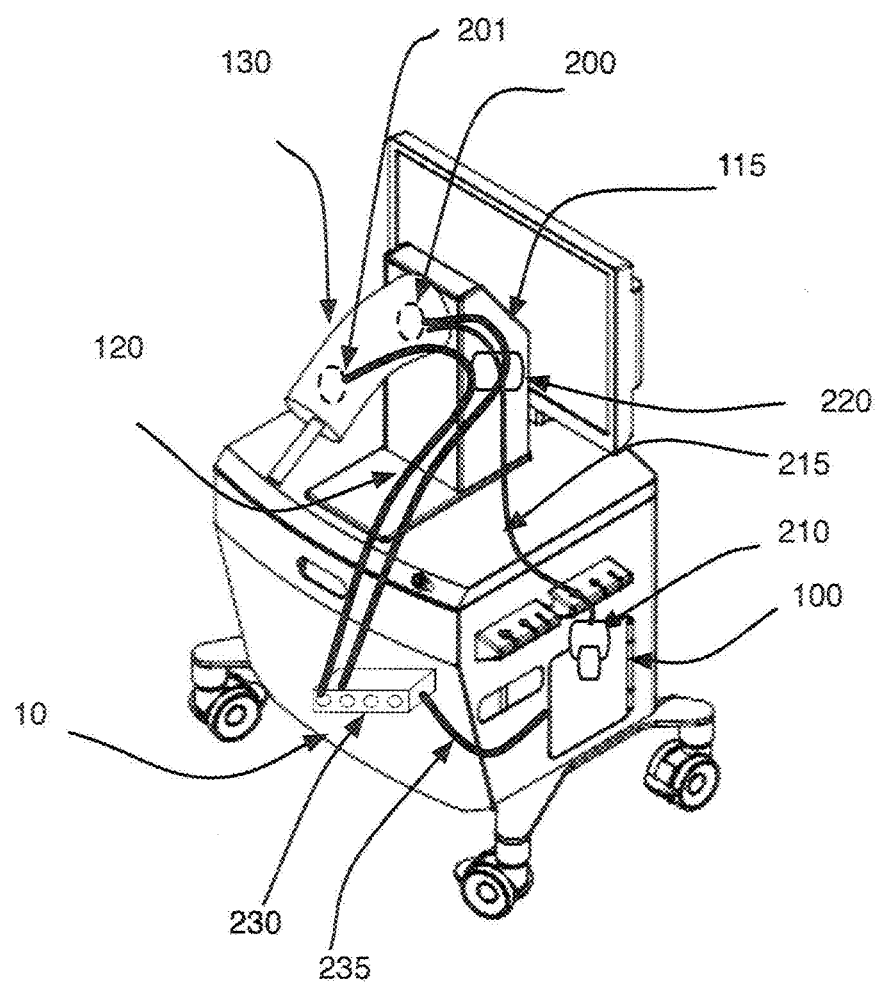
FIG. 2A illustrates a partial cutaway view of a medical simulation cart hosting an anatomy model according to an embodiment of the invention.
Figure 2B:
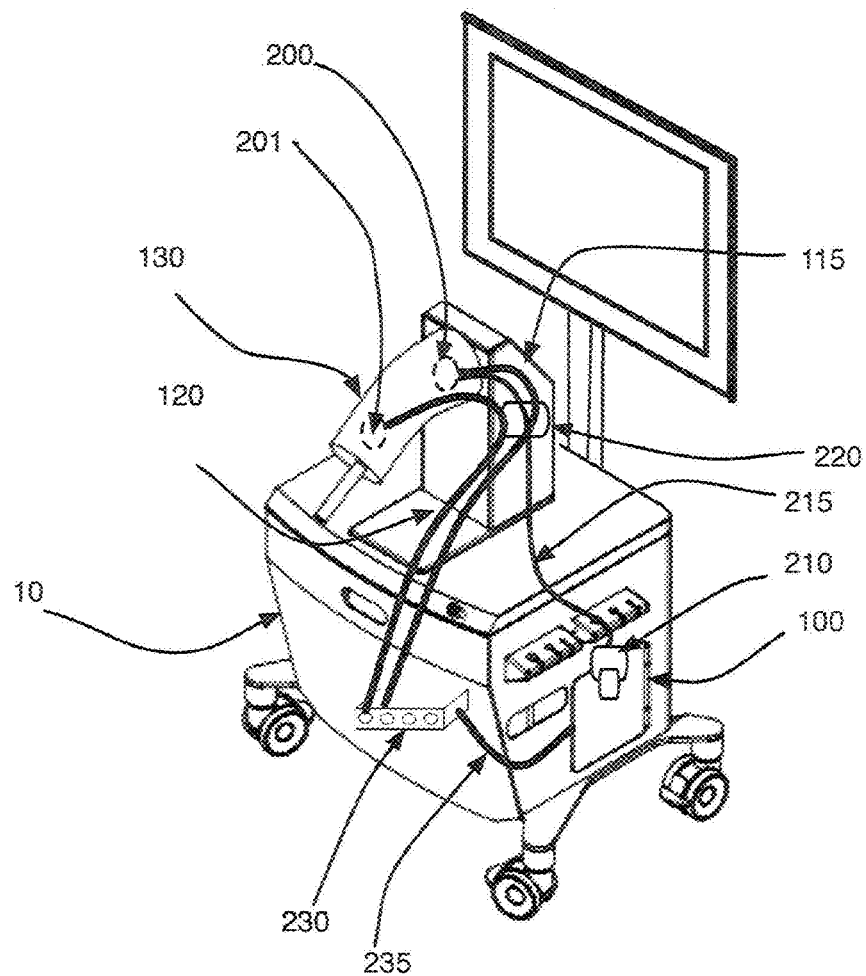
FIG. 2B illustrates a partial cutaway view of a medical simulation cart hosting an anatomy model according to an embodiment of the invention.

FIGS. 2A-2B depict a partial cutaway view of a medical simulation cart 10 hosting an anatomy model 130 according to an embodiment of the invention. Like FIGS. 1A-1B, FIG. 2A shows the medical simulation cart 10 with the display screen 110 in a lowered position, and FIG. 2B shows the medical simulation cart with the display screen 110 in a raised position. In FIGS. 2A-2B, the human anatomy model 130 comprises at least one position and orientation sensor 200 and at least one calibration unit 210 associated with the sensor 200. In FIGS. 2A-2B where a knee joint model 130 is illustrated, two position and orientation sensors 200, 201 are integrated in order to measure the position and orientation of the two main bones forming the knee joint, that is the tibia and the femur. For example, six degree of freedom ("6DOF") miniaturized magnetic tracking sensors 200, 201 may be mounted into the anatomy model 130, and a magnetic sensor transmitter unit 220 may be integrated into the mount 115 or directly into the anatomy model 130 (not illustrated). The magnetic sensor transmitter unit 220 may generate a magnetic field necessary for proper operation of the sensors 200, 201. The sensors 200, 201 may be substantially identical sensors so that interference from other fields or field distortion may be reduced or eliminated through common mode rejection. Substantially identical sensors may be sensors that are the same sensor model or have the same part number, for example. Each sensor 200, 201 may be connected to a tracking unit 230 through a dedicated communication link. In some embodiments the mount 115 may be fastened to the cart plug 120 in such a way that it is easily electrically connected in and disconnected out, for instance via a USB connection or other standard connection. Other embodiments are also possible, e.g. the tracking unit 230 can be integrated within the anatomic model 130 and/or the mount 115.

The tracking unit 230 may receive the sensor information and transmit it to the data processing unit 100 through a connection 235 such as a USB link, other standard connection, or other communication link. The data processing unit 100 may use the tracking unit 230 inputs to calculate the virtual anatomy model 130 position and orientation in accordance with the sensor 200, 201 measurement. The data processing unit 100 may use the calculated model 130 position and orientation to generate a visual model and display the visual model onto the display screen 110.

As known to those skilled in the art, the VR/AR model may be aligned with the anatomy model based on assumptions on the anatomy model actual position and orientation e.g. relative to the transmitter, and a sensor may be attached to the moving part of the anatomy model only, so that an absolute position and orientation of the VR/AR model can be derived by the VR/AR simulator. This solution is subject to drifts and instability due to, for instance, magnetic field distortion induced by a metal object or other electrical medical appliances in the close area of the VR/AR simulator. Thus, highly accurate tracking, which may be useful for some applications such as knee arthroscopy simulation, may require regular, cumbersome calibration of the sensors in the daily training room practice. In embodiments described herein, a relative, over-defined position and orientation of the model may be determined by calculating the location of at least one reference sensor 200 attached to the fixed part of anatomy model 130. When the anatomy model 130 also includes moving parts, the reference sensor 200 may complement the sensors that are used to track each moving part of the model, for instance the knee sensor 201 attached to the moving part of anatomy model 130.

In FIGS. 2A-2B, the tracking unit 230 may detect the position of sensor 201 to track the moving tibia part of the anatomy model 130 and the position of sensor 200 to track the fixed femur part of the knee model 130. Depending on the mechanical properties and ergonomic constraints of the anatomy model 130, various alternative mount positions may be chosen for sensors 200 and 201. Consequently, each sensor 200, 201 may have a different position and orientation relative to the other fixed parts of the anatomy model 130. For instance sensor 201 may have been attached at various places along the tibia bone in the case of the knee joint of FIGS. 2A-2B depending on how the model 130 has been manufactured, and sensor 201 may have a different position and orientation relative to the femur bone in the knee mode 130 of FIGS. 2A-2B and the tracking unit 230.

The resulting calibration data may therefore differ from one anatomy model 130 to another. In the case of the knee joint depicted on FIGS. 2A-2B, depending on how the anatomy model 130 is positioned when attached to the mount 115, the initial VR/AR model display generated by the data processing unit 100 may have to show a different leg flexion and varus-valgus angle matching the actual anatomy model 130 position and orientation. Prior accurate knowledge of the actual sensor 200, 201 positioning with regards to the anatomy model 130 bones, that is the sensor calibration, may be used to accurately determine the position and orientation of the VR/AR model. In the example of the knee model 130, accuracy in the order of magnitude of less than 1 mm in the 6DOF positioning may be observed, instead of up to 1 cm erroneous measurement experienced in other passive feedback solutions.

In accordance with the embodiments described herein, at least one sensor 200 may be integrated into the fixed part of the anatomy model 130. In addition, for models 130 including at least one moving part, at least one sensor 201 may be integrated within movable parts of the model 130. For example, each rigid part of the anatomy model 130 that moves relatively to another rigid part in that particular model 130, such as the tibia bone relative to the fixed femur bone in the knee arthroscopy case, may have its own sensor 201. Within the anatomy model 130, the tissues and the parts of the organs that are subject to different pathology case modeling, such as various shapes of ligaments and meniscus, may be simulated by various different VR/AR models corresponding to different types of patients, for instance an adult or a child, and/or different pathologies training cases. In addition, the position and orientation of the rigid and non-rigid structures without sensors 201 can also be interpolated based on information from other known structures, therefore the choice and placement of sensors 201 can be chosen according to accuracy and cost requirements of the given application.

In some embodiments, the sensor calibration data may be pre-computed at the time of sensor 200, 201 integration into the anatomy model 130 in accordance with the target VR/AR simulation model and stored into a calibration unit 210 associated with the anatomy model 130. In the case of the knee joint depicted in FIGS. 2A-2B, sensor 200 data may correspond to the fixed femur bone position and orientation as mounted onto the vertical mount 115 and sensor 201 data may correspond to the flexible tibia bone whose position and orientation is variable relative to the fixed femur. The calibration unit 210 may comprise storage and communication elements to store the sensor 200, 201 calibration data and/or transmit the sensor 200, 201 calibration data to the data processing unit 100.

For example, the calibration unit 210 may be implemented as a USB dongle configured to be connected to the sensor 201 via an electrical connection 215 such as a wire and plugged into data processing unit 100. The USB dongle calibration unit 210 may also be connected to the data processing unit 100 only or to the sensor 201 only. Other embodiments are possible as well, for instance the calibration unit 210 may be directly integrated into the anatomy model 130 and connected to the data processing unit 100 through the electrical fastening of the mount 115 onto the cart plug 120, or through an electrical fastening of the cart plug 120 itself, or through a wireless connection between the calibration unit 210 and the data processing unit 100.

The data processing unit 100 may compute the VR/AR model position and orientation by combining the absolute sensor measurement received from tracking unit 230 with the pre-computed calibration data from the calibration unit 210 matching the simulated VR/AR model. While in FIGS. 2A-2B the calibration unit 230 is represented as a separate unit from the model 130, in alternate embodiments it may be part of the model 130. In some embodiments in which the calibration unit 230 is integrated with the model 130, calibration data from the calibration unit 230 and from the sensor(s) 200, 201 may be transmitted over the same medium (e.g., the same physical wire(s) or same wireless frequency(ies)) and/or may be transmitted by the same transmitter.

In some embodiments, for example when the calibration unit 210 does not communicate directly with the data processing unit, the tracking unit 230 may store and transmit the anatomy model 130 identification from the calibration unit 210 to the data processing unit 100 so that the data processing unit 100 can automatically determine which model has been mounted onto the VR/AR simulation cart and propose a choice of matching VR/AR simulation training scenarios accordingly. The identification may comprise a model type, version, and serial number. For example, the proposed scenario may be displayed on the display 110, and a user may select the proposed scenario or a different scenario via the touchscreen or other interface.

It may be possible to simulate a number of different procedures over a physical model in a highly realistic way by further appending standard medical tools onto the VR/AR simulator cart of FIGS. 2A-2B, as will now be described in more detail with reference to FIGS. 3A-3B.

Figure 3A:
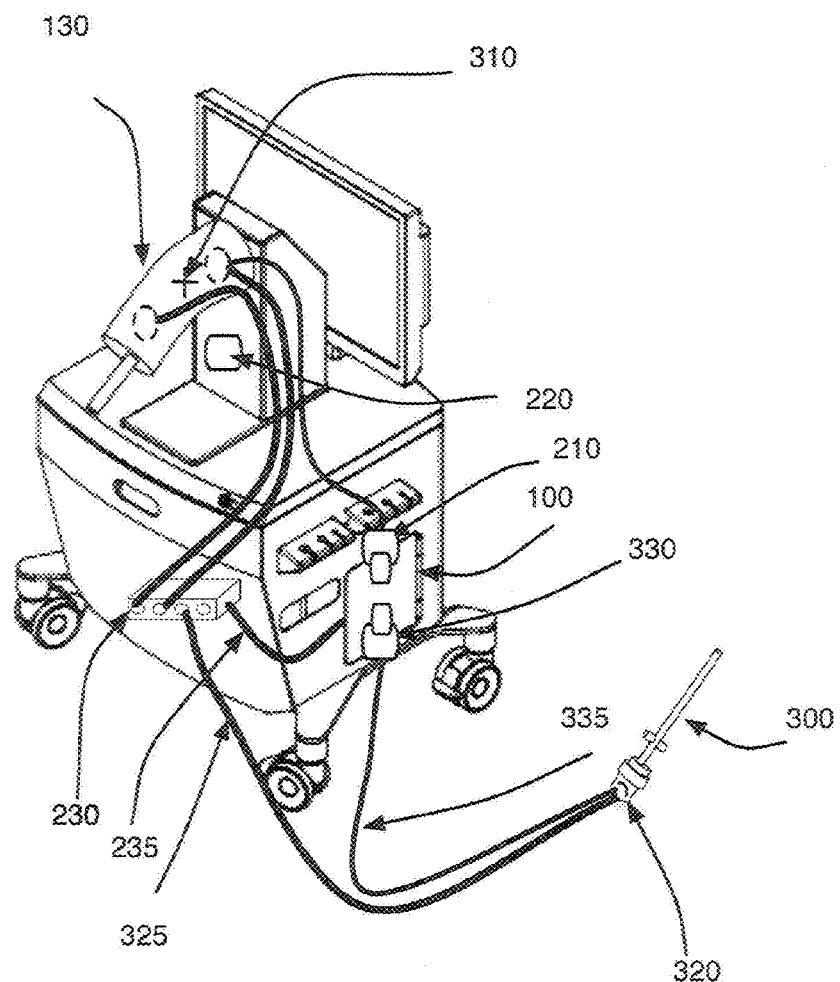
FIG. 3A illustrates a partial cutaway view of a medical simulation cart hosting an anatomy model and at least one medical tool according to an embodiment of the invention.
Figure 3B:
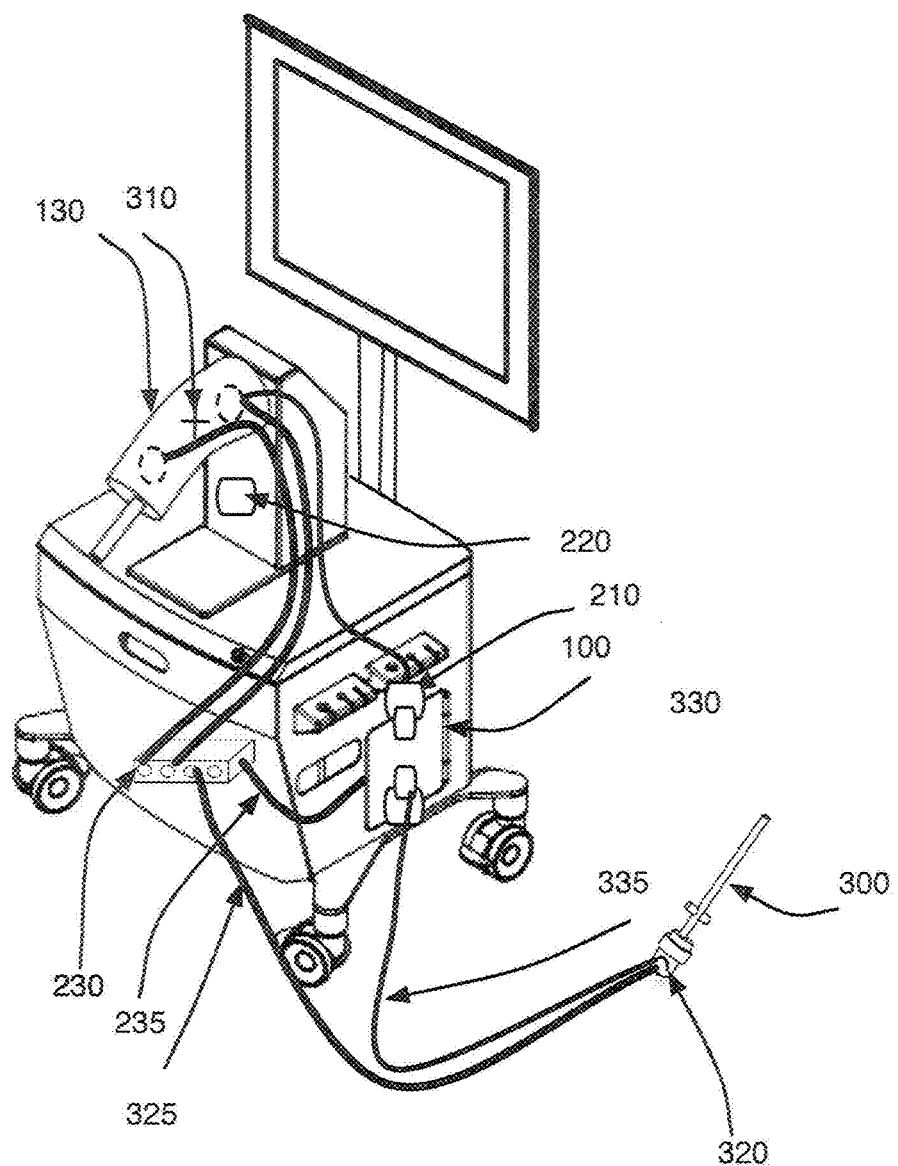
FIG. 3B illustrates a partial cutaway view of a medical simulation cart hosting an anatomy model and at least one medical tool according to an embodiment of the invention.

FIGS. 3A-3B show a medical tool 300 appended to the medical simulation cart of FIGS. 2A-2B. Like FIGS. 1A-1B and 2A-2B, FIG. 3A shows the medical simulation cart 10 with the display screen 110 in a lowered position, and FIG. 3B shows the medical simulation cart with the display screen 110 in a raised position. In many medical procedure simulations at least one imaging tool may be needed, for instance to simulate a diagnosis operation by allowing exploration of the organ. Examples of imaging tools may include endoscopes that are inserted directly into the organ by a natural orifice or through a small incision or imaging probes such as ultrasound probes that can also be used externally. For the purpose of illustration, in the case of a knee joint arthroscopy simulation, the medical tool 300 of FIGS. 3A-3B may be an arthroscope that can be inserted into the joint anatomy model 130 through a portal 310. The portal 310 may be chosen among known medical portals such as, in the case of the knee, the antero-medial portal, the antero-lateral portal, the dorso-medial portal, the dorso-lateral portal, the supramedial portal, or the dorso-supralateral portal. In some embodiments, the imaging tool 300 may be a standard operation room tool suitable for various medical procedures, for instance an arthroscope indifferently suitable for knee, shoulder, or elbow endostopy, that may be adapted to comprise at least one position and orientation sensor 320 and one calibration unit 330 associated with sensor 320. Depending on the anatomic model used, the portal or portals 310 might not be needed, for instance when a natural orifice can be used, or might be already incorporated in the models, or might be created by the operator at any convenient position.

The tool sensor 320 may be connected to the tracking unit 230 through a dedicated link 325. The tracking unit 230 may receive the sensor information and transmit it to the data processing unit 100 through a standard connection 235 such as a USB link or via some other communication channel. The data processing unit 100 may use the tracking unit 230 inputs to calculate the virtual anatomy model position and orientation in accordance with the model sensor 200, 201 measurement and the tool sensor 320 measurement respectively. The data processing unit 100 may use the calculated model 130 position and orientation to generate a visual model and display the visual model onto the display screen 110.

Physical parts of the anatomy model 130 that can be moved independently along at least one degree of freedom may require accurate tracking to avoid real world collisions of the tool with the anatomy model during the training manipulation, according to the various possible VR/AR models corresponding to different patients and different pathologies. Therefore, a sensor 201 may be integrated into each part of the anatomy model 130 that can be moved independently. It may be useful to provide as accurate a measurement as possible of the relative positions and orientations of the sensors 201 with regard to the physical model parts. This accuracy may be achieved by pre-calibrating each sensor 201.

As known to one skilled in the art, initial alignment of the VR/AR model with the position and orientation of the tool may also require calibration. For instance, in the case of the knee joint and arthroscope depicted in FIGS. 3A-3B, depending on how the anatomy model is positioned in the beginning, and how and where the arthroscope is inserted into the anatomy model 130 through portal 310, the initial VR/AR model display may show a different leg flexion and varus-valgus angle matching the actual anatomy model position on the one hand and the endoscope camera simulated field of view on the other hand. In some embodiments, calibration data may be pre-computed at a time when the sensor 320 is initially adapted onto the tool 300, and stored into a calibration unit 330 associated with the tool sensor 320. The standard operation room tool 300 may be one that is useable in real medical procedures, and may therefore not be initially constructed with an orientation sensor 320 and calibration unit 330. The orientation sensor 320 and/or calibration unit 330 may therefore be incorporated into the tool 300 after tool 300 manufacture, and the calibration may be performed at this time. Other tools 300 may be dedicated training tools which may be constructed with a built-in orientation sensor 320 and/or calibration unit 330, and calibration may be performed at construction time. For example, some expensive tools such as cameras may be simulated by non-functional training tools. In the case of the arthroscope 300 depicted in FIGS. 3A-3B, the sensor 320 is shown mounted at the handside end of the arthroscope 300, but depending on the mechanical properties and ergonomic constraints of the tool, various alternative mount positions may be chosen, for instance at the tip of the tool. The resulting calibration data, which may define the proximity of the sensor to the tool components such as the tip or working element, may differ accordingly.

The calibration unit 330 may comprise memory and communication elements 335 which may be configured to store the calibration data and/or transmit the calibration data to the data processing unit 100.

The calibration unit 330 may also store the tool 300 identification and/or transmit the tool 300 identification to the data processing unit 100 so that the data processing unit 100 can automatically determine and simulate an appropriate tool. For example, the tool identification may comprise a tool 300 type and tool 300 manufacturer information. Additional tool 300 identification information may be supplied as well, such as a tool 300 version or model number. In addition, the calibration unit 330 may also store parameters characterizing the behavior of the tool 300 (e.g. cutting speed in case of an arthroscopic shaver) and appearance of the tool 300, such as the geometric data, volumetric and surface models, texture information, and any other information useful to describe the tool in the VR/AR simulation.

In a possible embodiment as shown by FIGS. 3A-3B, the calibration unit 330 may be implemented as a USB dongle to be plugged into data processing unit 100. While in FIGS. 3A-3B the calibration unit 330 is represented as a separate unit from the tool 300, in alternate embodiments it may be part of the tool 300. In some embodiments in which the calibration unit 330 is integrated with the tool 300, calibration data from the calibration unit 330 and from the sensor 320 may be transmitted over the same medium (e.g., the same physical wire(s) or same wireless frequency(ies)) and/or may be transmitted by the same transmitter.

At run-time in the training room, the data processing unit 100 may compute the VR/AR model position and orientation by combining the absolute sensor measurement received from tracking unit 230 with the pre-computed recorded calibration data from the calibration units 210, 330 matching the actual simulated VR/AR model.

Figure 4:
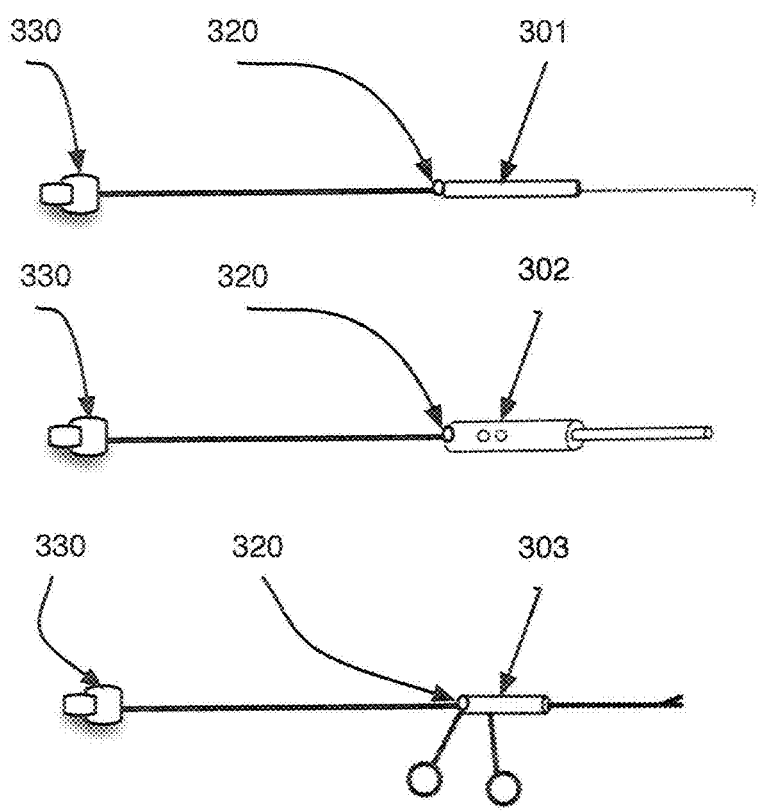
FIG. 4 illustrates a set of medical tools adapted to comprise at least one sensor and a calibration unit according to an embodiment of the invention.

The combination of sensor and calibration unit disclosed above for the anatomy model and the imaging tool respectively can be generalized to any type of medical tool suitable for medical procedure simulation training. FIG. 4 illustrates sample tools that may be adapted to comprise a position and orientation sensor 320 and a calibration unit 330 with storage, processing, and communication elements to handle the position and orientation calibration data of said sensor 320. These sample tools include a hook to push and pull tissue 301, a shaver 302, and a grasp handle 303. Other tools, not illustrated herein, can be adapted as well, such as a palpation hook, various types of punches (straight, slightly bent up, bent up, bent left, bent right and 90°), a grasp, a shaver hand-piece with flow control, a foot pedal entity, a pump, an ECG or EEG monitoring probe, etc.

Some medical tools may be equipped with buttons or various mechanical interaction elements which may be manipulated by the end user, for instance a foot pedal or an imaging tool zoom. In some embodiments, for proper VR/AR modeling and rendering, the tool 300 may report the real-time user interaction information to the data processing unit 100 through the calibration unit 330, in addition to the tool identifier and calibration data.

Other embodiments of the described VR/AR simulation cart, tools and system are also possible. Various sensor technologies may be used, such as the magnetic 6DOF tracking sensors suitable for medical use as supplied for instance by the Ascension manufacturer, or optical tracking sensors. The sensors 200, 201, 320 may be directly connected to the data processing unit 100 without a sensor transmitter unit 220 or tracking unit 230. When magnetic tracking sensors are used, the transmitter unit 220 may be mounted directly into the anatomy model 130, the mount 115, or the cart. When optical tracking sensors are used, a camera rather than a transmitter unit may be used and may be mounted in different places. For example, the camera may be placed far enough above the VR/AR simulator cart to allow the optical tracking sensors to substantially remain in the camera's field of view during the training manipulation. Some or all connections described herein may be wired or wireless, for instance by means of power efficient wireless standards such as Zigbee. In particular, wireless communication may be used for adapting medical tools already using wireless connectivity in the operation room. In many cases it may be desirable to use sensors measuring all six degrees of freedom of position and orientation, in certain cases it may be possible to use simpler sensors measuring less than six degrees of freedom, for instance in a case where the anatomy model is constrained in a certain position and/or orientation dimension it may be possible to measure a single degree of freedom such as a rotation angle.

In one embodiment, one calibration unit may be associated with each sensor. In other embodiments, one calibration unit may store and transmit the calibration data for at least two sensors. In some embodiments, the sensors 200, 201, 320 and the calibration units 210, 330 may be combined into a single unit that may be mounted onto the physical anatomy model, the mount, or the tool. Although depicted as separate in the above illustrations, any of the calibration unit 210, the sensor transmitter unit 220, the tracking unit 230, and the data processing unit 100 may also be combined.

The VR/AR simulation apparatus, systems, and methods described herein may enable the setup and operation of a multi-purpose training room, as will become more apparent from the description of VR/AR simulation initialization methods. Various medical training scenarios can be simulated using the same multi-purpose VR/AR simulation cart by mounting, with reference to FIGS. 2A-2B, the anatomy model 130 and mount 115 corresponding to the target medical training scenarios onto the simulation cart plug 120, connecting the anatomy model sensors 200, 201 to the tracking unit 230, and connecting the calibration unit 210 to the data processing unit 100. Further medical training scenarios can be simulated using the same multi-purpose VR/AR simulation cart by further connecting, with reference to FIGS. 3A-38 and FIG. 4, the tool sensor 320 to the tracking unit 230 and the tool sensor calibration unit 330 to the data processing 100 for each relevant medical tool 300, 301, 302, 303, according to the target scenario. It therefore may be possible for an apprentice physician to train on different anatomy models, different medical tools and different medical procedures using the same VR/AR simulation system cart, without requiring substantial hardware setup and calibration process by skilled personnel for each different training scenario.

Moreover, when new anatomy models or medical tools become available to be integrated into the training room, it may be possible to order a newly adapted model or medical tool from a training simulator provider and connect it to the VR/AR simulation cart without requiring on site specialized personnel for initial setup and training, in particular in terms of calibration of the VR/AR modeling. In accordance with the embodiments described herein, the new model or tool may be adapted and configured off-site by pre-calibration and be delivered to the training room operator with its "plug-and-train" pre-computed recorded calibration data. In addition, if appearance and behavior of the tool is stored together with the calibration data, simulating new tools without changing the data processing unit or simulation software may be possible.

Figure 5:
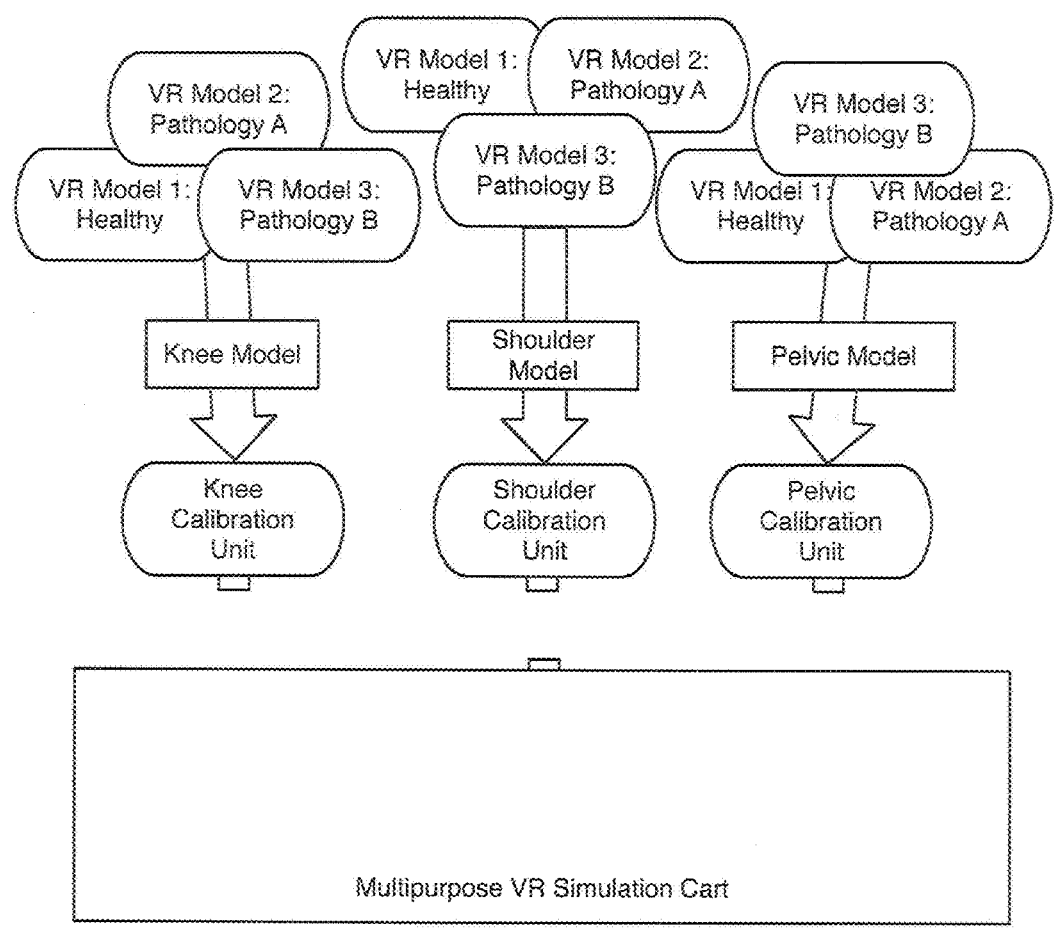
FIG. 5 illustrates a number of different VR/AR medical training use cases according to an embodiment of the invention.

FIG. 5 depicts a number of different VR/AR medical training use cases according to an embodiment of the invention. As shown in FIG. 5, various pathologies can be further simulated with different VR/AR simulations models and various combinations of physical anatomy models and tools, for instance knee arthroscopy, shoulder arthroscopy, and pelvic endoscopy, with the same multipurpose VR/AR simulation cart 10. The data processing unit 100 may identify an attached anatomy model 130 and tools 300, 301, 302, 303 from their respective calibration unit identification data, select a choice of possible VR/AR training scenarios matching said model and tools, and display the choice as a graphical menu onto the display screen 110 for the user to select a scenario. For instance, in the case of knee arthroscopy, various sizes of knee joints, variable articular cartilage lesions, a partially or fully torn cruciate ligament, various meniscus tears, hypertrophy of Hoffa's fat pad, etc., may be simulated. In advanced scenarios, the user can virtually repair the meniscus by cutting the torn meniscus parts, as well as any free-floating broken cartilage and bone parts met in various pathologies, with the grasp tool, replicating the gesture of extracting from the anatomy model virtually cut meniscus pieces or free-floating parts. In practice, tissue, cartilage, and bone pieces (floating/connected) may be obscuring a view, and this scenario may be rendered for highly realistic simulation scenarios. To this end, the data processing unit 100 may compute the appearance and the behavior of the ligaments in the simulated joint, for example in order to simulate damaged or worn ligaments, in accordance with the measured movement of the knee model (flexion, varus-valgus), the arthroscope, and related calibration data. In some embodiments, the data processing unit 100 may highlight a selected pathology scenario region of interest by rendering it onto the display screen 110 with a different color, texture, or highlighted contour. While the above examples are described specifically for the knee arthroscopy case, they may also apply to other joint arthroscopy pathologies and medical simulation applications in general. The user may manually select a scenario using the touchscreen, a mouse, the keyboard, a switch or a combination of any those. Other controls may also be used, such as for instance vocal control.

A VR/AR simulation system setup and operation method according to an embodiment of the invention will now be described in more detail. First, the user or setup operator may mechanically plug one of the interchangeable anatomy models 130 either directly or by its vertical mount 115 onto the medical simulation cart plug 120, connect the anatomy model sensor 200, 201 to the tracking unit 230 and connect the anatomy model calibration unit 210 to the data processing unit 100. The operator may further connect each relevant medical simulation tool sensor 320 to the tracking unit 230 and each tool calibration unit 330 to the data processing unit 100. In other embodiments, the setup according to the user selection may also be automatized.

Figure 6:
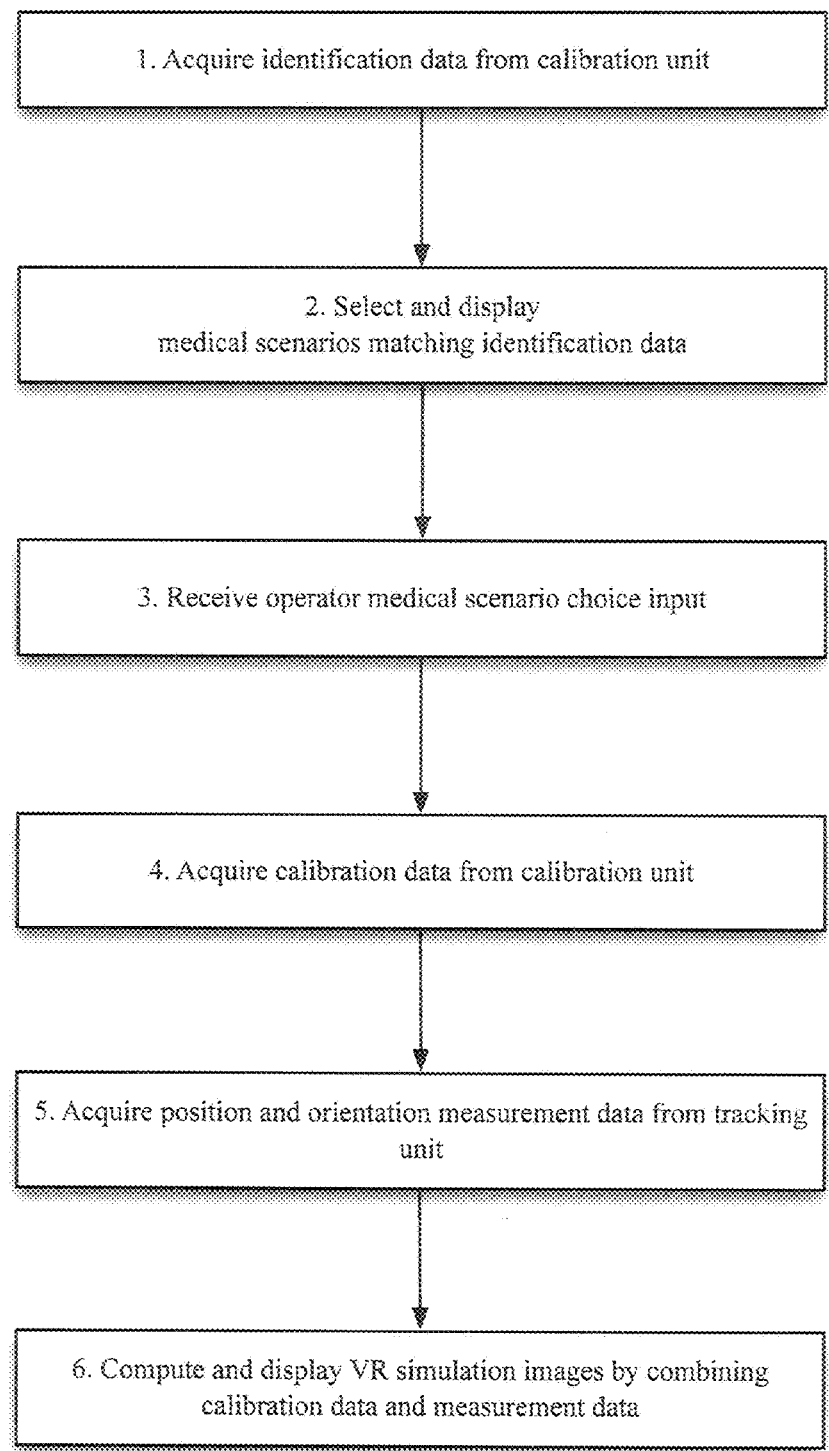
FIG. 6 illustrates a flow chart of a self-calibration method according to an embodiment of the invention.

FIG. 6 represents a flow chart of a self-calibration method according to an embodiment of the invention.

In step 1, the data processing unit 100 may acquire the identifier data from each connected calibration unit 210, 330 to identify the connected anatomy model 130 and any connected medical simulation tool 300, 301, 302, 303. In step 2, the data processing unit 100 may select and display on the display screen 110 a choice of medical simulation scenarios matching the identified anatomy model and medical simulation tools. In step 3, the operator may select a medical simulation scenario and input the selection to the data processing unit 100 which may receive the selection. For example, a touch screen element of the display screen 110 may be used for input. In step 4, the data processing unit 100 may acquire the pre-computed calibration data from each connected calibration unit 210, 330 for each position and orientation sensor 200, 201, 320. In some embodiments, step 4 may be done at the same time as step 1. The data processing unit 100 may then be ready to compute and render the actual VR/AR simulation images. In step 5, the data processing unit 100 may begin computing and rendering the VR/AR simulation images by acquiring the orientation and position measurement data for each sensor connected to the tracking unit 230 in real time. In step 6, the data processing unit 100 may combine the orientation and position measurement data with the pre-computed calibration data for each sensor to determine the actual VR/AR simulation model position and orientation. For example, the pre-computed calibration data for each sensor may be a six degrees of freedom position and orientation vector offset measuring the sensor position and orientation relative to a fixed reference predefined on the physical anatomy model or medical tool, as relevant. In some embodiments additional tool interaction data may be input in real time by the calibration unit 320 to the data processing unit 100 in order to compute and render a hilly interactive VR/AR simulation scenario.

When all sensors are calibrated and can be tracked in real time, the VR/AR simulation that is rendered to the display 110 may substantially correspond to the real positions of the various models and tools being tracked. For example, if a user is manipulating a tool 300 and touches a bone within the model 130, the display 110 may show the tool 300 touching the bone at substantially the same instant and in substantially the same position of the actual contact. As noted above, accuracies on the order of millimeters may be possible.

In some embodiments, the data processing unit 100 may estimate the VR/AR model position and orientation by weighting over-defined model sensors' position and orientation measurements according to sensor measurement reliability. In some embodiments, a same weight may be given to the different sensors, so that the VR/AR model position and orientation may be measured as an average of the different estimates. A reduced weight may be allocated to a less reliable sensor, for instance when a magnetic tracking sensor may be more exposed to the magnetic field distortion due to its positioning within the VR/AR simulator anatomy model. A zero weight may be allocated in the extreme case of a dysfunctional sensor.

In some embodiments, beyond live rendering of the VR/AR simulation scenario, the data processing unit 100 may apply various additional processing, such as, but not limited to, recording and playing back the simulation, evaluating and ranking the trainee performance and progress, compiling training statistics, raising alarms, and highlighting certain scenarios or scenes to draw special attention from the end user.

In order to provide highly realistic simulation scenarios, a highly detailed rendering of the organ structure and texture corresponding to different pathologies, for instance flying pieces of tissues or broken bones or ligaments, or bleeding, may be desirable.

In a case where multiple sensors are combined with complex interactivity, for instance when simulating a use of a foot pedal to control a shaver tool flow pressure into an organ, the data processing unit 100 may not be able to compute and render the highly realistic images in real time due to the underlying VR/AR mathematical modeling complexity. To address this issue, a library of highly realistic images for the most likely scenarios may be pre-computed offline and stored in the data processing unit 100. The data processing unit 100 can then interpolate and render the actual images in real time by interpolating them from the library images and the actual model, sensor, and tool data inputs.

Other advanced applications of the proposed VR/AR simulation system may require the insertion of an external device into the anatomy model. One example of such an application is the simulation of the insertion of an intrauterine device ("IUD") into the womb through the cervix under ultrasound control, or the simulation of the insertion of a coronary stent under fluoroscopy guidance. In some embodiments the external device may be virtually simulated. In other embodiments, a real external device may be used. In the latter case a position and orientation sensor and calibration unit can be mounted to the external device in a similar manner to the tools and anatomical devices described above in order to accurately track it in the VR/AR simulation scenario.

Advanced scenarios may require more direct interaction with the anatomy model structures and tissue. For improved training realism, in some embodiments, it may be possible to combine the VR/AR simulation cart, tools, systems, and methods with haptic solutions such as force feedback actuators. For example, haptic simulation may be provided to enable a user to "feel" a body part with the tool that is not physically present within the model. The VR/AR display may show the haptically simulated body part at substantially the same time and in substantially the same position. Many example force feedback actuators may be known by those skilled in the art. In some embodiments, it may be possible to exploit and apply perceptual tricks to the VR/AR model simulation rendering so that the end user experiences different virtual anatomic structures within the same physical anatomy model structures.

While various embodiments have been described above, it should be understood that they have been presented by way of example and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments. Thus, the present embodiments should not be limited by any of the above-described embodiments.

In addition, it should be understood that any figures which highlight the functionality and advantages are presented for example purposes only. The disclosed methodology and system are each sufficiently flexible and configurable such that they may be utilized in ways other than that shown.

Although the term "at least one" may often be used in the specification, claims and drawings, the terms "a", "an", "the", "said", etc. also signify "at least one" or "the at least one" in the specification, claims and drawings.

Finally, it is the applicant's intent that only claims that include the express language "means for" or "step for" be interpreted under 35 U.S.C. 112, paragraph 6. Claims that do not expressly include the phrase "means for" or "step for" are not to be interpreted under 35 U.S.C. 112, paragraph 6.

What is claimed is:

1. A simulation system comprising:
a data processing unit;
a display in communication with the data processing unit; and
a physical model comprising:
an anatomy model;
a tool;
a position and orientation sensor configured and positioned to sense a position of the physical model, an orientation of the physical model, or a combination thereof; and
a calibration unit configured to store calibration data associated with the position and orientation sensor and the physical model; and
the data processing unit is configured to:
identify the physical model based on the calibration data and propose a choice of simulation scenarios based on the identification, each simulation scenario comprising a virtual reality (VR) model or an augmented reality (AR) model;
receive a selection of one of the simulation scenarios from a user;
receive data from the position and orientation sensor indicating the position of the physical model, the orientation of the physical model, or a combination thereof;
receive the calibration data from the calibration unit indicating a position of the position and orientation sensor relative to the physical model, an orientation of the position and orientation sensor relative to the physical model, or a combination thereof;
generate the VR model or AR model associated with the selected simulation scenario using the data from the position and orientation sensor and the calibration data from the calibration unit; and
render the VR model or AR model to the display.

2. The simulation system of claim 1, wherein the physical model comprises a fixed portion, and wherein the position and orientation sensor is attached to the fixed portion of the physical model.

3. The simulation system of claim 1, wherein the VR model or AR model comprises a virtual image.

4. The simulation system of claim 3, wherein the data processing unit is configured to combine the virtual image with an actual image to form an augmented reality image.

5. The simulation system of claim 1, wherein:
the physical model comprises a plurality of position and orientation sensors; and
the data processing unit is configured to:
receive data from each of the plurality of position and orientation sensors indicating a position of each of the position and orientation sensors relative to the physical model, an orientation of each of the position and orientation sensors relative to the physical model, or a combination thereof; and
generate the VR model or AR model using the data from each of the plurality of position and orientation sensors and the calibration data from the calibration unit.

6. The simulation system of claim 5, wherein each of the plurality of position and orientation sensors is substantially identical.

7. The simulation system of claim 5, wherein the physical model comprises a movable part, and at least one of the plurality of position and orientation sensors is disposed in the movable part.

8. The simulation system of claim 5, wherein the data processing unit is further configured to weigh the data from each of the plurality of position and orientation sensors in accordance with the data reliability.

9. The simulation system of claim 1, further comprising a mount configured to accept the physical model.

10. The simulation system of claim 1, further comprising a tracking unit in communication with the data processing unit, the tracking unit configured to receive the data from the position and orientation sensor and transmit the data from the position and orientation sensor to the data processing unit.

11. The simulation system of claim 1, wherein the position and orientation sensor is a magnetic sensor.

12. The simulation system of claim 11, further comprising a magnetic sensor transmitter unit configured to generate a magnetic field detectable by the position and orientation sensor.

13. The simulation system of claim 1, wherein the display is a touchscreen display.

14. The simulation system of claim 1, further comprising a cart to which the display is attached.

15. The simulation system of claim 1, wherein the data processing unit is configured to propose the choice of simulation scenarios using the data from the position and orientation sensor in addition to the calibration data from the calibration unit.

16. The simulation system of claim 15, wherein the data processing unit is configured to display the choice of simulation scenarios on the display.

17. The simulation system of claim 15, wherein the data processing unit is configured to generate a VR model or AR model corresponding to the physical model using the data from the position and orientation sensor, the calibration data from the calibration unit, and the selected simulation scenario.

18. The simulation system of claim 1, wherein:
the tool comprises:
a tool position and orientation sensor configured to sense a position of the tool, an orientation of the tool, or a combination thereof; and
a tool calibration unit configured to store calibration data associated with the tool position and orientation sensor and the tool; and
the data processing unit is configured to:
receive data from the tool position and orientation sensor indicating the position of the tool, the orientation of the tool, or a combination thereof;
receive the calibration data from the tool calibration unit indicating a position of the tool position and orientation sensor relative to the tool, an orientation of the tool position and orientation sensor relative to the tool, or a combination thereof;
generate a tool virtual image corresponding to the tool using the data from the tool position and orientation sensor and the calibration data from the tool calibration unit; and
render the tool virtual image to the display.

19. The simulation system of claim 18, wherein the position and orientation sensor and the tool position and orientation sensor are substantially identical.

20. The simulation system of claim 1, wherein the tool comprises a surgical tool.

21. The simulation system of claim 18, further comprising a tracking unit in communication with the data processing unit, the tracking unit configured to receive the data from the tool position and orientation sensor and transmit the data from the tool position and orientation sensor to the data processing unit.

22. The simulation system of claim 18, wherein the tool position and orientation sensor is a magnetic sensor.

23. The simulation system of claim 18, wherein the data processing unit is configured to propose the choice of simulation scenarios using the data from the tool position and orientation sensor in addition to the calibration data from the tool calibration unit.

24. The simulation system of claim 23, wherein the data processing unit is configured to display the choice of simulation scenarios on the display.

25. The simulation system of claim 23, wherein the data processing unit is configured to generate a tool virtual image corresponding to the tool using the data from the tool position and orientation sensor, the calibration data from the tool calibration unit, and the selected simulation scenario.

26. A simulation method comprising:
receiving, with a data processing unit, calibration data from a calibration unit indicating a position of a position and orientation sensor relative to a physical model, an orientation of a position and orientation sensor relative to a physical model, or a combination thereof, wherein the physical model comprises an anatomy model, a tool, the position and orientation sensor, and the calibration unit;
identifying, with the data processing unit, the physical model based on the calibration data and propose a choice of simulation scenarios based on the identification, each simulation scenario comprising a virtual reality (VR) model or an augmented reality (AR) model;
receiving, with the data processing unit, a selection of one of the simulation scenarios from a user;
receiving, with the data processing unit, data from the position and orientation sensor indicating a position of the physical model, an orientation of the physical model, or a combination thereof;
generating, with the data processing unit, the VR model or AR model associated with the selected simulation scenario using the data from the position and orientation sensor and the calibration data from the calibration unit; and
rendering, with the data processing unit, the VR model or AR model to a display.

27. The simulation method of claim 26, further comprising:
mechanically constraining, with a mount, a fixed portion of the physical model to a fixed position relative to the mount.

28. The simulation method of claim 26, wherein the VR model or AR model comprises a virtual image.

29. The simulation method of claim 28, further comprising:
combining, with the data processing unit, the virtual image with an actual image to form an augmented reality image.

30. The simulation method of claim 26, further comprising:
receiving, with the data processing unit, data from each of a plurality of position and orientation sensors indicating a position of each of the position and orientation sensors relative to the physical model, an orientation of each of the position and orientation sensors relative to the physical model, or a combination thereof; and
generating, with the data processing unit, the VR model or AR model using the data from each of the plurality of position and orientation sensors and the calibration data from the calibration unit.

31. The simulation method of claim 30, wherein each of the plurality of position and orientation sensors is substantially identical.

32. The simulation method of claim 30, wherein the data from each of the plurality of position and orientation sensors is weighted in accordance with the data reliability.

33. The simulation method of claim 26, further comprising:
receiving, with a tracking unit in communication with the data processing unit, the data from the position and orientation sensor; and
transmitting, with the tracking unit, the data from the position and orientation sensor to the data processing unit.

34. The simulation method of claim 26, further comprising generating, with a magnetic sensor transmitter unit, a magnetic field detectable by the position and orientation sensor.

35. The simulation method of claim 26, further comprising displaying, with the data processing unit, the choice of simulation scenarios on the display.

36. The simulation method of claim 26, further comprising generating, with the data processing unit, a VR model or AR model corresponding to the physical model using the data from the position and orientation sensor, the calibration data from the calibration unit, and the selected simulation scenario.

37. The simulation method of claim 26, further comprising pre-loading the calibration data from the calibration unit into the calibration unit before the calibration data from the calibration unit is received by the data processing unit.

38. The simulation method of claim 26, further comprising:
receiving, with a data processing unit, the calibration data from a tool calibration unit indicating a position of a tool position and orientation sensor relative to the tool, an orientation of a tool position and orientation sensor relative to a tool, or a combination thereof;
receiving, with the data processing unit, the data from the tool position and orientation sensor indicating the position of the tool, the orientation of the tool, or a combination thereof;
generating, with the data processing unit, a tool virtual image corresponding to the tool using the data from the tool position and orientation sensor and the calibration data from the tool calibration unit; and
rendering, with the data processing unit, the tool virtual image to a display.

39. The simulation method of claim 38, further comprising:
receiving, with a tracking unit in communication with the data processing unit, the data from the tool position and orientation sensor; and
transmitting, with the tracking unit, the data from the tool position and orientation sensor to the data processing unit.

40. The simulation method of claim 38, further comprising proposing, with the data processing unit, the choice of simulation scenarios a using the data from the tool position and orientation sensor in addition to the calibration data from the tool calibration unit.

41. The simulation method of claim 40, further comprising displaying, with the data processing unit, the choice of simulation scenarios on the display.

42. The simulation method of claim 40, further comprising generating, with the data processing unit, a tool virtual image corresponding to the tool using the data from the tool position and orientation sensor, the calibration data from the tool calibration unit, and the selected simulation scenario.

43. The simulation method of claim 38, further comprising pre-loading the calibration data from the tool calibration unit into the tool calibration unit before the calibration data from the tool calibration unit is received by the data processing unit.

* * * * *